US00PP16588P2

(12) United States Plant Patent
Goto et al.

(10) Patent No.: US PP16,588 P2
(45) Date of Patent: May 30, 2006

(54) ***PETUNIA* PLANT NAMED 'TEMARI'**

(50) Latin Name: *Petunia hybrida*
Varietal Denomination: Temari

(76) Inventors: Koji Goto, 730-3-2-101, Endo, Fujisawa City, Kanagawa Prefecture (JP); Fusako Goto, 151, Okada, Samukawa, Koza, Kanagawa Prefecture (JP); Susumu Goto, 151, Okada, Samukawa, Koza, Kanagawa Prefecture (JP)

( * ) Notice: Subject to any disclaimer, the term of this patent is extended or adjusted under 35 U.S.C. 154(b) by 143 days.

(21) Appl. No.: 10/990,883

(22) Filed: Nov. 17, 2004

(51) Int. Cl.
*A01H 5/00* (2006.01)

(52) U.S. Cl. ..... Plt./356
(58) Field of Classification Search ..... Plt./356
See application file for complete search history.

*Primary Examiner*—Kent Bell
(74) *Attorney, Agent, or Firm*—Jondle & Associates P.C.

(57) ABSTRACT

A *Petunia* cultivar particularly distinguished by a purple flower with a dark purple edge, decumbent growth habit and small flower diameter.

1 Drawing Sheet

Genus and species: *Petunia hybrida.*
Variety denomination: 'Temari'.

BACKGROUND OF THE NEW PLANT

The present invention comprises a new and distinct cultivar of *Petunia,* botanically known as *Petunia hybrida,* and hereinafter referred to by the cultivar name 'Temari.' It is characterized by having a purple flower with a dark purple edge, decumbent growth habit and small flower size. The new cultivar originated from a hybridization made in Kanagawa, Japan in 1995. The female parent was a *Petunia* line of Brazilian origin, unnamed, with red, pink and white flowers and the male parent was an unknown, unnamed *Petunia* breeding line. From 1996 to 2000, evaluations of single-plant selections from the F1 progeny of the initial cross were performed. In 2000, a single-plant selection from those evaluations was hybridized with a different *Petunia* breeding line (unnamed). The hybridization took place in Kakegawa, Japan.

F1 seed from the final hybridization was evaluated and one F1 line was selected based on its purple flower with a dark purple edge, decumbent growth habit and small flower size. The line was then asexually propagated through plant cuttings in both Kanagawa, Japan and Salinas, Calif. The line was further evaluated in the greenhouse from 2001 through 2003 to establish the uniformity and stability of its characteristics. The line has been shown to reproduce true to type in successive generations of asexual propagation.

DESCRIPTION OF PHOTOGRAPHS

This new *Petunia* plant is illustrated by the accompanying photographs which show the plant form, foliage and flowers, the colors shown being as true as can be reasonably obtained by conventional photographic procedures.

Figure 1:
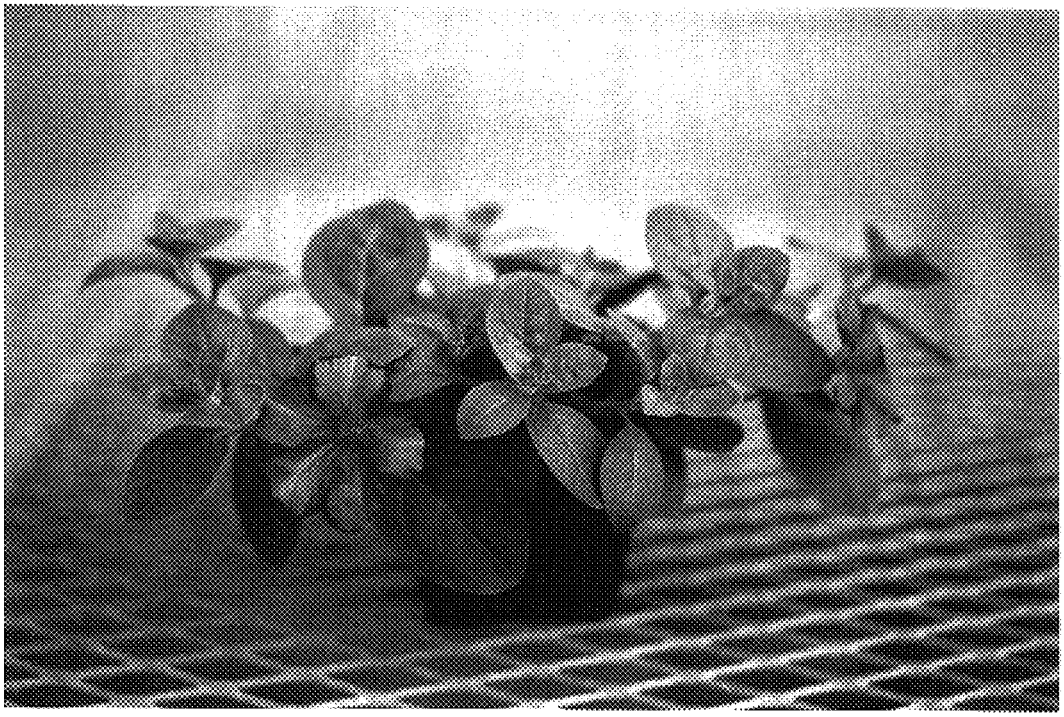

FIG. 1. shows overall plant habit.

Figure 2:
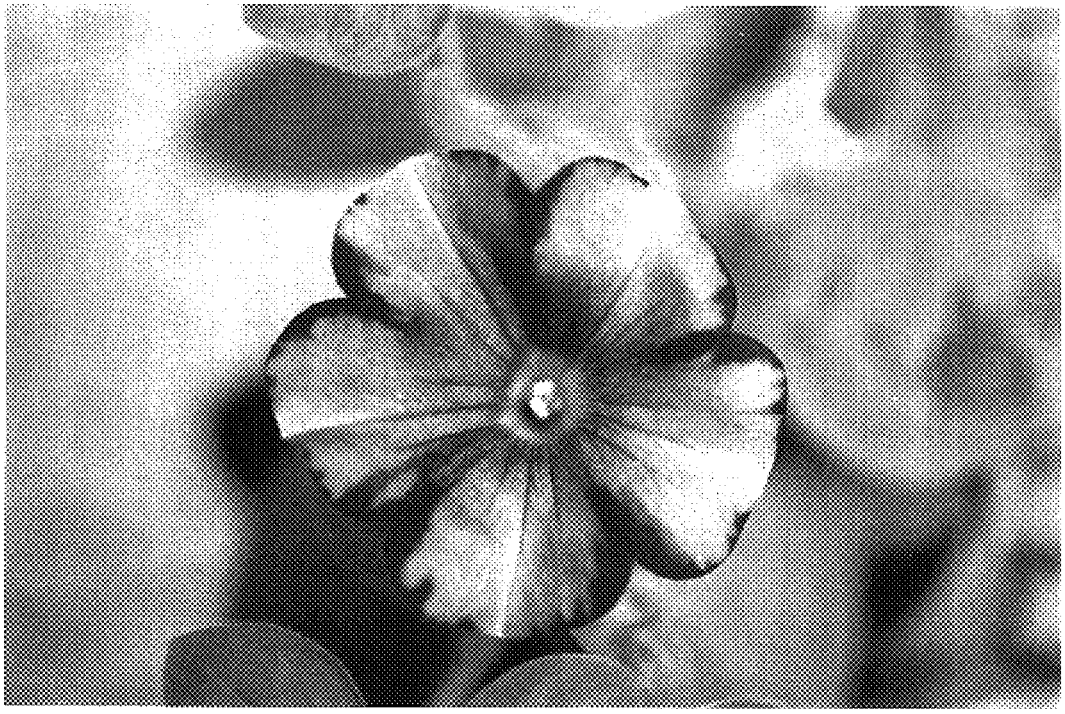

FIG. 2. shows the mature inflorescence.

DESCRIPTION OF THE NEW CULTIVAR

The following detailed description sets forth the distinctive characteristics of 'Temari'. The data which define these characteristics were collected from asexual reproductions carried out in Kanagawa, Japan. The detailed description was taken from plants grown under greenhouse conditions for approximately 4 months from transplanting of rooted cuttings. Color references are to The R.H.S. Colour Chart of The Royal Horticultural Society of London (R.H.S.), 4$^{th}$ Edition.

DETAILED BOTANICAL DESCRIPTION

Classification:
- *Family.*—Solanaceae.
- *Species.*—*Petunia hybrida* f. cv. 'Temari'.
- *Common name.*—*Petunia.*

Parentage:
- *Male.*—Unknown *Petunia* breeding line of unknown origin (unnamed).
- *Female.*—Unknown *Petunia* line of Brazilian origin (unnamed).

Plant description:
- *Life cycle.*—Tender Perennial.
- *Form.*—Decumbent (trailing).
- *Habit.*—Freely branching.
- *Height.*—9.3 cm as measured from soil level to top of plant.
- *Spread.*—62.3 cm.

Propagation:
- *Type cuttings.*—Vegetative cuttings.
- *Time to produce a rooted cutting.*—4–5 weeks.
- *Time to bloom from propagation.*—4–6 weeks after root development.
- *Root description.*—1 main taproot with many fine branches, RHS 155A (white).
- *Root habit.*—Freely branching.

Environmental conditions for plant growth: Plants were propagated from vegetative cuttings and grown individually in 15 cm diameter plastic pots in a glass greenhouse located in Salinas, Calif. Pots contained a peat mossbased growing medium. Soluble fertilizer containing 18% nitrogen, 8% phosphorus and 18% potassium was applied in four daily irrigations. The fifth irrigation was made with non-fertilized water. Pots were top-dressed with a slow-release fertilizer containing 18% nitrogen, 8% phosphorous and 18% potassium. The typical average air temperature was 24 C.

Stems:

*Stem color.*—RHS 145C (yellow-green).
*Stem diameter.*—3.5 mm.
*Stem length.*—About 2.0 cm from soil line to first node.

Lateral branches:

*Number.*—About 4 per plant.
*Length.*—58.3 cm.
*Diameter.*—2.0–3.0 mm.
*Internode length:* 5.2 cm.
*Texture.*—Densely pubescent.
*Anthocyanin color.*—None observed.
*Color.*—RHS 144A (yellow-green).

Leaves:

*Leaf arrangement*—Alternate.
*Leaf shape*—Obovate.
*Leaf apex.*—Mucronate.
*Leaf base.*—Attenuate.
*leaf margin.*—Entire.
*Leaf surface.*—Densely pubescent.
*Venation.*—Pinnate.
*Leaf length:* 5.2 cm.
*Leaf width.*—4.9 cm.
*Leaf color.*—Upper surface: RHS 137A (green). Lower surface: RHS 138C (green).
*Petiole length:* 7 mm.
*Petiole diameter:* 2 mm at branch, 5 mm at base of leaf.
*Petiole color: RHS* 143B (green).

Inflorescence:

*Flowering habit.*—Many blooms per plant; flowers face all directions; flowers and buds produced concurrently.
*Flower type.*—Single, one flower per peduncle; 5 petals arranged circularly and roughly bell-shaped.
*Flowering requirements.*—Late Spring through early Fall seasons; greater than 12 hours of light per day; temperature above 13° C.
*Duration of flowers.*—About 5 days.
*Fragrance.*—Slight.

Corolla description:

*Bud length.*—3.1 cm.
*Bud diameter.*—1 mm.
*Bud shape.*—Ovoid to cylindrical.
*Flower depth.*—4 cm.
*Flower tube length.*—2.8 cm.
*Flower tube diameter.*—1 cm.
*Flower diameter.*—5.6 cm.
*Petal shape.*—Spatulate.
*Petal length.*—2.1 cm.
*Petal width.*—2.6 cm.
*Petal apex.*—Mucronate.
*Petal margin.*—Entire, crinkled.
*Petal texture.*—Glabrous.
*Petal color.*—Upper surface: RHS 67C (red-purple) with RHS 74A (purple) edge. Lower surface: RHS 186D (grayed-purple) with RHS 155A (white) midvein streak, RHS 186B (grayed-purple) edges, and RHS 144B (yellow-green) midvein and veins.
*Corolla tube color.*—Inner: RHS 78C (purple) with RHS 77A (purple) veins. Outer: RHS 18D (grayed-purple) with RHS 144B (yellow-green) midvein and RHS 77A (purple) veins.

Calyx description:

*Arrangement.*—5 sepals circularly arranged at base of corolla.
*Length.*—1.4 cm.
*Width.*—3 mm.
*Shape.*—Ovate.
*Apex.*—Mucronate.
*Base.*—Bottom ¼ of sepals are fused; cuneate shape above fuse point.
*Margin.*—Entire.
*Texture.*—Densely pubescent.
*Color.*—Upper surface: RHS 137A (green). Lower surface: RHS 137C (green).

Peduncle description:

*Length.*—2.5 cm.
*Diameter.*—3 mm.
*Texture.*—Densely pubescent.
*Color.*—RHS 141A (green).

Reproductive organs:

*Stamen number.*—5, arranged adjacent to pistil.
*Anther length.*—1.6 cm.
*Pollen color.*—RHS 155A (white).
*Pistil number.*—1 per inflorescence.
*Pistil length.*—1.8 cm.
*Stigma color.*—RHS 144C (yellow-green).
*Style length.*—1.7 cm.
*Style color.*—144D (yellow-green).
*Ovary.*—Superior.

Disease and Insect Resistance

No unique or distinguishing resistance or susceptibility to common *Petunia* pathogens or pests observed.

Comparison with Known Cultivars

*Petunia* 'Temari' is a unique variety of *Petunia* due to its purple flower with a dark purple edge, decumbent growth habit and small flower diameter. 'Temari' is most similar to the *Petunia* variety 'Kakegawa S59' (U.S. Plant Pat. No. 13,979); however, there are differences as noted in Table 1 below.

TABLE 1

| Characteristic | 'Temari' | 'Kakegawa S59' |
|---|---|---|
| Petal color, upper surface | RHS 67C (red-purple) with RHS 74A (purple) edge | RHS 74B (red-purple) |
| Petal color, lower surface | RHS 186D (grayed-purple) with RHS 186B (grayed-purple) edges, RHS 144B (yellow-green) midveins and veins, and RHS 155A (white) midvein streak | RHS 73A (red-purple) |
| Inner corolla tube color | RHS 78C (purple) with RHS 77A (purple) veins | RHS 73C (red-purple) |
| Outer corolla tube color | RHS 18D (grayed-purple) with RHS 77A (purple) veins and RHS 144B (yellow-green) midvein | RHS 69C with 141C (green) veins |
| Flower diameter | 5.6 cm | 6.0–7.0 cm |

'Temari' is distinguished from its female parent, unknown *Petunia* line of Brazilian origin (unnamed), mainly by flower color. 'Temari' has a red-purple flower with a dark purple edge while the unnamed female parent has red, pink and white flowers. A comparison with the male parent, unknown *Petunia* breeding line of unknown origin (unnamed), is not possible because the male parent is unknown.

We claim:

1. A new and distinct cultivar of *Petunia* plant as shown and described herein.

* * * * *